United States Patent [19]

Aziz

[11] 4,324,247

[45] Apr. 13, 1982

[54] DISPOSABLE ABSORBENT ARTICLE HAVING AN ABSORBENT CORE AND A TOPSHEET

[75] Inventor: Mohammed I. Aziz, Cincinnati, Ohio

[73] Assignee: The Procter & Gamble Company, Cincinnati, Ohio

[21] Appl. No.: 148,900

[22] Filed: May 12, 1980

[51] Int. Cl.³ ............................................. A61F 13/16
[52] U.S. Cl. ................................. 128/287; 128/290 R; 128/290 W
[58] Field of Search ............... 128/287, 290 R, 290 W

[56] References Cited

U.S. PATENT DOCUMENTS

| | | | |
|---|---|---|---|
| 3,929,135 | 12/1975 | Thompson | 128/287 |
| 3,945,386 | 3/1976 | Anzurowski et al. | 128/287 |
| 3,965,906 | 6/1976 | Karami | 128/284 |
| 3,994,299 | 11/1976 | Karami | 128/284 |
| 4,041,951 | 8/1977 | Sanford | 128/287 |

FOREIGN PATENT DOCUMENTS 2406525  8/1974  Fed. Rep. of Germany ...... 128/287

*Primary Examiner*—P. Ives
*Attorney, Agent, or Firm*—John M. Pollaro; Fredrick H. Braun; Richard C. Witte

[57] ABSTRACT

A disposable absorbent article having improved strike-through and rewet characteristics is disclosed. The disposable absorbent article has an embossed and perforated thermoplastic film interposed between the topsheet and the absorbent core. The topsheet, likewise, is embossed. The combination of the embossed topsheet and the embossed and perforated thermoplastic film permit liquid to rapidly penetrate the topsheet while preventing liquid in the absorbent core from flowing from the absorbent core back to the topsheet.

1 Claim, 5 Drawing Figures

U.S. Patent    Apr. 13, 1982    4,324,247
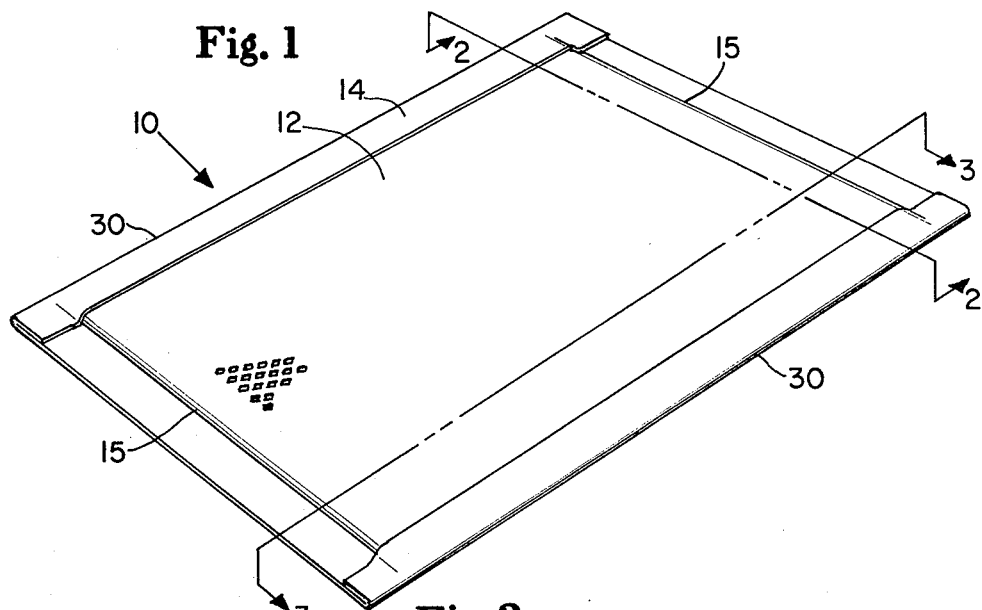
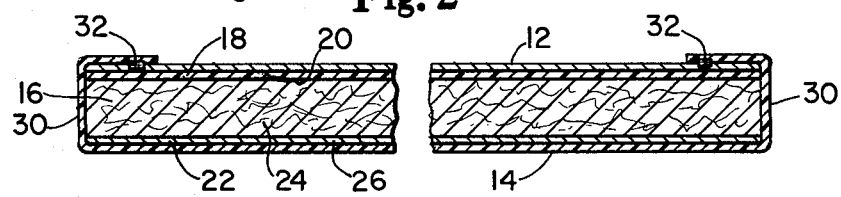
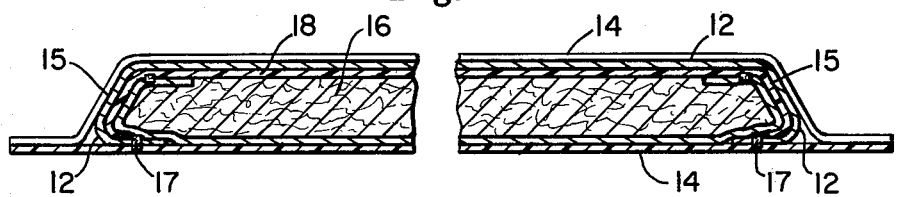
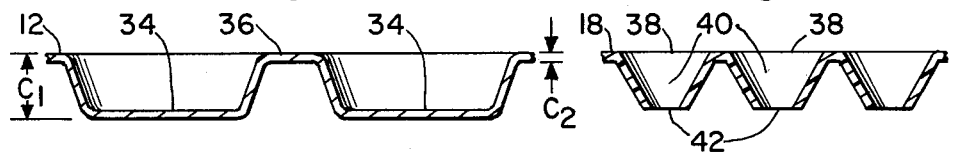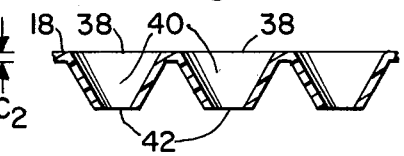

DISPOSABLE ABSORBENT ARTICLE HAVING AN ABSORBENT CORE AND A TOPSHEET

BACKGROUND OF THE INVENTION

This invention relates to disposable absorbent structures generally, and more particularly relates to disposable diapers and the like. Still more particularly, this invention relates to disposable diapers having an embossed film interposed between a topsheet and an absorbent core.

Infants and incontinent adults are usually clothed in a diaper or diaper-like garment which is capable of absorbing and containing human waste products. Diapers are garments which are drawn up between the legs and fastened about the waist of the wearer and are well known. Such garments may be manufactured from reusable woven cloth materials and worn in conjunction with a fluid-impermeable outer garment. In recent years, however, disposable diapers have come into widespread use and have gained a high degree of acceptance as a consumer product. Disposable diapers are designed to combine a fluid-impermeable outer garment with a disposable absorbent core, forming an integral structure which is intended to be discarded after a single use. As used herein, the term "diaper" includes absorbent structures suitable for use by incontinent adults as well as by infants.

A major in-use problem encountered with diapers, both reusable and disposable, is leakage of waste product which contaminates clothing articles that contact the diaper, such as pants, shirts, and bedding. The amount of leakage experienced by a diaper wearer can be reduced by improving the rate at which the liquid enters the absorbent core. Thus, a diaper in which the liquid rapidly penetrates the topsheet and is contained in the absorbent core will experience less leakage than a diaper in which liquid is able to run across the topsheet before penetrating into the absorbent core. Reducing run-off, therefore, reduces the amount of leakage experienced with the diaper.

Another in-use problem associated with diapers is the dryness of the skin contacting surface. Generally, the drier the skin contacting surface, the more comfortable the diaper. There have been several patents directed towards reducing the surface wetness in disposable diaper structures. U.S. Pat. No. 3,965,906 entitled ABSORBENT ARTICLE WITH PATTERN AND METHOD which issued to Hamzeh Karami on June 29, 1976 and U.S. Pat. No. 3,994,299 entitled ABSORBENT ARTICLE which issued to Hamzeh Karami on Nov. 30, 1976 both teach a diaper structure having a perforated thermoplastic film interposed between the topsheet and the absorbent core. Likewise, U.S. Pat. No. 3,945,386 entitled DISPOSABLE DIAPER which issued to Edward Anczurowski on Mar. 23, 1976 discloses a diaper having a perforated plastic film between the topsheet and the absorbent core.

The prior art teachings, however, lack the aspects of the present invention whereby reduced surface run-off and improved rewet characteristics are obtained by providing a fluid pervious thermoplastic film embossed with tapered capillaries between an embossed topsheet and an absorbent core.

It is therefore an object of the present invention to provide a disposable diaper having reduced surface run-off characteristics.

A further object of the present invention is to provide a disposable diaper having improved surface dryness characteristics.

A still further object of the present invention is to provide a disposable diaper having a thermoplastic film embossed with a multiplicity of tapered capillaries interposed between an embossed topsheet and an absorbent core.

Other objects of the present invention will become more fully apparent in the following description of the embodiments of this invention and from the appended claims.

SUMMARY OF THE INVENTION

According to the present invention, a disposable diaper is manufactured having an absorbent core encased between a fluid-pervious topsheet and a fluid-impervious backsheet. In addition, an embossed and perforated thermoplastic film is interposed between the topsheet and the absorbent core.

The topsheet is embossed with a multiplicity of depressions and retains its undulating characteristic under normal compressive loadings. Further, the embossing of the topsheet is accomplished without any densification of any portion of the topsheet.

The embossed and perforated thermoplastic film has a multiplicity of tapered capillaries which transport liquid from the topsheet to the absorbent core and prevent liquid from flowing in the reverse direction. The resulting diaper exhibits improved leakage and surface dryness characteristics.

BRIEF DESCRIPTION OF THE DRAWINGS

FIG. 1 is a perspective view of the disposable diaper of the present invention.

FIG. 2 is a cross-sectional edge view taken along line 2—2 of FIG. 1.

FIG. 3 is a cross-sectional end view taken along line 3—3 of FIG. 1.

FIG. 4 is an edge view of the topsheet of the present invention.

FIG. 5 is an edge view of the intermediate layer of the present invention.

DESCRIPTION OF THE PREFERRED EMBODIMENTS

Referring now to the figures, there is shown a preferred embodiment of the present invention as it would be used in a disposable diaper. As used herein, the term "disposable" refers to articles which are intended to be discarded after a single use (i.e., they are not intended to be laundered or otherwise restored and reused), while the term "diaper" refers to a garment generally worn by infants and incontinent persons which is drawn up between the legs and fastened about the waist of the user. It should be understood, however, that the present invention is also applicable for use in other disposable absorbent articles such as bandages, bed pads, catamenials, and the like.

FIG. 1 shows an unfolded, rectangular, disposable diaper 10 prior to its being placed on a diaper wearer (not shown). As best seen in FIG. 2, a preferred disposable diaper 10 basically comprises topsheet 12, backsheet 14, absorbent core 16, and intermediate layer 18.

Absorbent core 16 is generally compressible, conformable, non-irritating to the wearer's skin, and is capable of absorbing and retaining liquids. A preferred absorbent core 16 has first and second opposed faces 20 and 22, respectively, and comprises an absorbent layer 24 and a tissue layer 26 which forms second opposed face 22. Absorbent layer 24 may be manufactured in a wide variety of sizes and shapes (e.g., rectangular, hourglass, etc.) and from a wide variety of liquid absorbent materials commonly used in disposable absorbent articles, such as comminuted wood pulp, generally referred to as airfelt. Other liquid absorbing materials can also be used for absorbent layer 24, such as a multiplicity of plies of crepe, cellulose wadding, absorbent foams or sponges, or any equivalent material. Further, the size and absorbent capacity of absorbent layer 24 may be varied to accommodate wearers ranging from infants to adults. The preferred embodiment illustrated in FIG. 1 is rectangular and is intended for infants from about 12 pounds to about 23 pounds (about 5 kgs. to about 10 kgs.). Absorbent layer 24 is, therefore, a pad of airfelt approximately 12 inches (31.8 cm.) wide by 16 inches (40.6 cm.) long having an absorbent capacity of about 14 gm. of water.

Tissue layer 26 improves the tensile strength of absorbent core 16 and reduces the tendency of absorbent layer 24 to lump or ball when wetted. Tissue layer 26 also helps improve lateral wicking of absorbed liquids, thereby providing a more even distribution of liquids throughout absorbent core 16. While a number of materials and manufacturing techniques may be used to manufacture tissue layer 26, satisfactory results have been obtained with a sheet of tissue paper having a basis weight of from about 12 pounds per 3,000 sq. ft. (19 grams per sq. cm.) and having an air permeability of about 100 cu. ft. per minute per sq. ft. (30.5 cubic meters per minute per sq. meter) over a ½ inch (12.8 mm.) water pressure drop. While tissue layer 26 is preferably coterminus with absorbent layer 24, it may have different dimensions, a different configuration, or it may be omitted entirely.

Backsheet 14 is impervious to liquids and is preferably manufactured from a thin plastic film, although other flexible liquid impervious materials may also be used. Backsheet 14 prevents liquid contained in absorbent core 16 from wetting articles which contact the diaper, such as bed sheets and undergarments. Polyethylene films having a thickness of from about 0.001 to about 0.002 inches (0.0025 to 0.0051 cm.) have been used for backsheet 14 in a preferred embodiment with satisfactory results. As used herein, the term "flexible" refers to materials which are compliant and which will readily conform to the general shape and contours of the human body.

Backsheet 14 is superimposed on second opposed face 22 of absorbent core 16 and extends beyond the edges thereof. Longitudinal sides 30 of backsheet 14 are folded onto and affixed to topsheet 12 along longitudinal seams 32 in any suitable manner such as by the use of adhesives. A suitable adhesive is manufactured by National Starch Corp. of Bridgewater, N.J. and marketed under the tradename Instant Lok 34-2933, although other adhesives as are well known may also be used. A more detailed description of how topsheet 12, backsheet 14, and absorbent core 16 may be assembled into a disposable diaper is given in U.S. Pat. No. Re. 26,151 entitled DISPOSABLE DIAPER which issued to Robert C. Duncan et al. on Jan. 31, 1967, said patent being incorporated herein by reference.

In a preferred embodiment, topsheet 12 is superimposed on first opposed surface 20. Topsheet 12 is coterminous with the longitudinal sides of absorbent core 16 but is longer than absorbent core 16. As best seen in FIG. 3, transverse edges 15 of topsheet 12 are folded onto second opposed surface 22 of absorbent core 16 and affixed to backsheet 14 along transverse seams 17. Absorbent core 16 is, therefore, encased between backsheet 14 and topsheet 12.

Topsheet 12 is compliant, soft-feeling and non-irritating to the wearer's skin. Further, topsheet 12 is liquid permeable, permitting liquids to readily penetrate through its thickness. A suitable topsheet 12 may be manufactured from a wide range of materials such as natural fibers (e.g., wood or cotton fibers), synthetic fibers (e.g., polyester, polypropylene) or a combination thereof.

A particularly preferred topsheet 12 comprises about 65% staple length polyester fibers having a denier of about 1.5, such as Kodel type 411 polyester fibers marketed by Tennessee Eastman Corporation of Kingsport, Tenn.; about 15% staple length crimped rayon fibers having a denier of approximately 1.5; and about 20% acrylic copolymer binder such as Celanese CPE-8335 marketed by Celanese Corporation of Charlotte, N.C. As used herein, the term "staple length fibers" refers to those fibers having a length of at least ⅝ inches (15.9 mm.).

Clearly, there are a number of manufacturing techniques which may be utilized to manufacture topsheet 12. For example, topsheet 12 may be woven, nonwoven, spunbound, carded, or the like. A preferred topsheet 12 is carded, saturated with a binder solution, dried and cured by means well known to those skilled in the art. Preferably, topsheet 12 has a basis weight range of from about 18 to about 22 grams per square yard and a true caliper $c^2$ as shown in FIG. 4, of from about 7 to about 15 mils (about 0.18 to about 0.38 mm.) when measured under a load of about 200 pascals. As used herein, the term "true caliper" refers to the thickness of topsheet 12 as measured between the parallel surfaces and is most conveniently measured on a sheet of material which has been neither creped nor embossed as shown in FIG. 4. Preferred topsheet 12 is further characterized by a minimum wet tensile strength of at least about 400 grams per centimeter in the machine direction and at least about 55 grams per centimeter in the cross machine direction.

Still referring to FIG. 4, it can be seen that topsheet 12 has a multiplicity of depressions 34 which impart an embossed caliper $C^2$ of from about 13 to about 25 mils (about 0.33 to about 0.64 mm.) to topsheet 12. As used herein, the term "embossed caliper" refers to the thickness of topsheet 12 as measured between parallel planes passing through the remotest points at either surface of topsheet 12 under a load of about 200 pascals. Depressions 34 preferably constitute between about 10% and about 50% of the surface area of upper surface 36 of topsheet 12. Upper surface 36 is the surface of topsheet 12 which contacts the diaper wearer. Upper surface 36 maintains its undulating characteristic under normal use loadings. In other words, when used in diaper 10, upper surface 36 generally retains its shape when the diaper wearer, for example, sits on topsheet 12.

Depressions 34 may be formed in topsheet 12 by utilizing any of several processes as are well known in the art. For example, depressions 34 may be formed by embossing or vacuum forming techniques. Several methods for forming depressions 34 are described in detail in U.S. Pat. No. 4,041,951 entitled ABSORPTIVE STRUCTURE HAVING IMPROVED SUR- FACE DRYNESS AND IMPROVED RESISTANCE TO REWETTING IN USE, issued to Lawrence H. Sanford on Aug. 16, 1977, which patent is incorporated herein by reference. The process used to form depressions 34 does not, however, densify any portion of topsheet 12.

Intermediate layer 18 is interposed between topsheet 12 and absorbent core 16. In the preferred embodiment, intermediate layer 18 is coterminus with the longitudinal sides of absorbent core 16, but is longer than absorbent core 16. As best seen in FIG. 3, transverse edges 19 of intermediate layer 18 are folded onto second opposed surface 22 of absorbent core 16 and affixed to topsheet 12 in any suitable manner such as by ultrasonic bonding about its periphery.

Referring now to FIG. 5, it can be seen that intermediate layer 18 has a plurality of tapered capillaries 40, each of which has a base opening 38, and an apex opening 42. Apex opening 42 is in intimate contact with absorbent core 16 and depressions 34 are in contact with base openings 38. Further, base openings 38 and apex openings 42 are spaced apart from each other so as to form tapered capillaries 40.

Intermediate layer 18 is manufactured from a liquid impervious material such as low density polyethylene film having a thickness of from 0.001 to 0.002 inches (0.0025 to 0.0051 cm.). The liquid impervious material is provided with a multiplicity of tapered capillaries 40 in a manner, size, configuration, and orientation set forth in U.S. Pat. No. 3,939,135 entitled ABSORPTIVE STRUCTURE HAVING TAPERED CAPILLARIES, which issued to Hugh A. Thompson on Dec. 30, 1975, which patent is incorporated herein by reference.

Diaper 10 exhibits improved strikethrough times and rewet values. Strikethrough time is a measure of the time liquid takes to penetrate through the topsheet 12. Rapid penetration of the topsheet 12 (i.e., low strikethrough time) is important to reduce the possibility of liquid running over the surface of topsheet 12 and leaking from the sides.

Strikethrough may be determined using any suitable procedure. The data presented in Table I was generated using the following general procedure.

The strikethrough time of a topsheet 12 may be determined using any suitable procedure which will measure the time it takes for liquid to penetrate the topsheet 12. The following procedure has been used with good results.

A 5 inch by 5 inch (12 cm.×12 cm.) sample of topsheet 12 is placed over a 4 inch by 4 inch (10 cm.×10 cm.) absorbent core which has preferably been conditioned or stored at 73° F. (24° C.) and 50% relative humidity to help eliminate variations in the data due to varying moisture contents of the absorbent cores. The absorbent core of the test sample is comminuted wood pulp weighing from 2.4 to 3.0 grams and having a density of from 0.7 to 8.5 grams/cubic cm. A 4 inch×4 inch (10 cm.×10 cm.) plate weighing 800 grams and having an 0.25 inch (6.3 mm.) diameter hole centered therein is placed on the topsheet 12. The hole traverses the thickness of the plate and is filled with 5 ml of a liquid having a surface tension of about 47 dynes. The time required for the 5 ml of liquid to penetrate the top-sheet 12 is the strikethrough time. The shorter the strike-through time, the better the strikethrough characteristics of the topsheet 12. The rewet value is a measure of the amount of liquid which flows from the absorbent core 16 to the outer surface of the topsheet 12. Large quantities of liquid on the outer surface of the topsheet 12 (i.e. high rewet values) are undesirable because they lead to the discomfort of the wearer of the disposable absorbent article.

The rewet value of a disposable absorbent article may be determined using any suitable procedure. A procedure which was used with good results will now be described.

A 5 inch by 5 inch (12×12 cm.) test sample is prepared and is preferably conditioned or stored at 73° F. (24° C.) and 50% relative humidity to help eliminate variations in data due to varying moisture contents of the samples as hereinbefore described. A quantity of liquid is discharged onto the topsheet of the test samples and allowed to penetrate into the absorbent core (e.g. 4.8 ml/g. of absorbent material. To assure even distribution of the liquid within the absorbent core, the test sample is subjected to a pressure of about 0.50 psi (3.5 kilopascals) for about 3 minutes. The required pressure may be generated simply by placing a weight on the test sample. The weight is removed and two pieces of pre-weighed absorbent paper such as Whatman No. 4 filter paper are placed on the topsheet of the test sample. The weight is dried to remove any liquid from it and placed on the absorbent papers which have been placed on the test sample. After about 2 minutes, the absorbent papers are removed and reweighed to determined the quantity of liquid they have absorbed. The quantity of liquid absorbed by the absorbent papers is the rewet value of the sample tested.

Several test samples of differing constructions were prepared and tested to determine both their strike-through time and rewet value. The results of these tests are presented in Table I. As can be seen from Table I, Sample 1 exhibited both a low strikethrough time and a low rewet value. Samples 3–4 all exhibited rewet values and strikethrough times higher than those of sample 1.

TABLE I

Rewet and Strikethrough characteristics of Various Diaper Constructions[1]

| Sample | Diaper Construction | Strikethrough Time (sec.) | Rewet Value (g) |
|---|---|---|---|
| 1 | Embossed topsheet[2] with tapered capillary intermediate layer[3] | 0.5 | 0.12 |
| 2 | Non-embossed topsheet[4] with tapered capillary intermediate layer[3] | 0.9 | 0.35 |
| 3 | Embossed topsheet[2] without an intermediate layer | 0.7 | 1.41 |
| 4 | Non-embossed topsheet[4] without an intermediate layer | 0.9 | 1.67 |

Footnotes:
[1]The absorbent core for each diaper construction tested was a 4 × 4 inch (10 cm × 10 cm) pad of comminuted wood pulp weighing approximately 2.4–3.0 grams and having a density of 0.070–0.085 g/cm$^3$.
[2]The embossed topsheet used was carded polyester having a basis weight of 15 g/sq. meter and an embossed caliper of 0.018 inches (0.046 cm) at 0.03 psi (200 pascals) such as is manufactured by Scott Paper Company of Rodgers, Arkansas and marketed under the tradename 4-176. The depressions in the embossed topsheet used were spaced about 0.20 inches (0.5 cm) apart in the machine direction and about 0.17 inches (0.43 cm) apart in the cross machine direction.
[3]The intermediate layer used had an apex opening of about 0.015 inches (0.04 cm.) and a base opening of about 0.040 inches (0.10 cm).
[4]The non-embossed topsheet used had the same basic characteristics as the embossed topsheet.

It will be understood by those skilled in the art that the invention has been described with reference to an exemplary preferred embodiment and that variations and modifications can be effected in the described embodiment without departing from the scope and spirit of the invention.

For example, the intermediate layer 18 may be provided with tapered capillaries 40 only in the crotch portion of diaper 10 (i.e., the central portion of diaper 10) while the end portions at each end of diaper 10 are liquid impervious. Further, an envelope tissue may be interposed between intermediate layer 18 and absorbent core 16.

What is claimed is:

1. A disposable diaper comprising:
  an absorbent core means for absorbing liquids, said absorbent core means having first and second opposed faces;
  a liquid impervious backsheet, said backsheet being superimposed on said second opposed face of said absorbent core means;
  a liquid permeable topsheet, said topsheet being superimposed on said first opposed face of said absorbent core means and said topsheet being affixed to said backsheet, said absorbent core means being encased between said topsheet and said backsheet, said topsheet being a non-woven material which is generally hydrophobic and having a multiplicity of depressed areas provided substantially throughout the entire surface of said topsheet, said depressed areas comprising between about 10 percent and about 50 percent of the total surface area of said topsheet, as measured in the plane of said depressed areas, said topsheet having a multiplicity of non-depressed areas surrounding said depressed areas, said non-depressed areas contacting the wearer's skin in use, said depressed areas and said non-depressed areas being of substantially uniform density; and
  an intermediate layer interposed between said topsheet and said absorbent core means, said intermediate layer having a multiplicity of tapered capillaries, each of said capillaries having a base in the plane of said topsheet and an apex remote from said plane of said topsheet having an angle of taper of from about 10° to about 60°, having base opening dimensions of from about 0.006 to about 0.250 inches and having apex opening dimensions of from about 0.004 to about 0.100 inches, said apex opening being in intimate contact with said absorbent core means and said base openings being in intimate contact with said depressed areas of said topsheet; said intermediate layer having a crotch portion and first and second end portions; said crotch portion having a multiplicity of said capillaries and said first and second end portions being liquid impermeable.

* * * * *

UNITED STATES PATENT AND TRADEMARK OFFICE
CERTIFICATE OF CORRECTION

PATENT NO. : 4,324,247
DATED : April 13, 1982
INVENTOR(S) : MOHAMMED I. AZIZ

It is certified that error appears in the above–identified patent and that said Letters Patent are hereby corrected as shown below:

Column 4, line 29 , "spunbound" should read
-- spunbonded --.

Column 6, line 16, "material." should read --material). --.

Signed and Sealed this

Eighth Day of November 1983

[SEAL]

Attest:

GERALD J. MOSSINGHOFF

Attesting Officer     Commissioner of Patents and Trademarks